(12) United States Patent
James

(10) Patent No.: US 6,608,208 B1
(45) Date of Patent: *Aug. 19, 2003

(54) PROCESS FOR THE PREPARATION OF 1,2-BENZISOTHIAZOLIN-3-ONES

(75) Inventor: Mark Robert James, Manchester (GB)

(73) Assignee: Zeneca Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/298,923

(22) Filed: Apr. 26, 1999

Related U.S. Application Data

(63) Continuation of application No. 08/875,075, filed as application No. PCT/GB96/00427 on Feb. 26, 1996, now Pat. No. 5,936,094.

(30) Foreign Application Priority Data

Mar. 17, 1995 (GB) .............................................. 9505377

(51) Int. Cl.[7] ........................................... C07D 275/04
(52) U.S. Cl. ..................................................... 548/209
(58) Field of Search ......................................... 548/209

(56) References Cited

U.S. PATENT DOCUMENTS 4,736,040 A  4/1988  Tonne et al. ................ 548/209

FOREIGN PATENT DOCUMENTS

| EP | 187 349 | 7/1986 |
|---|---|---|
| GB | 848 130 | 9/1960 |
| WO | 94/20479 | 9/1994 |

OTHER PUBLICATIONS

Tyrrell: "Synthesis of Bunte Salts from 1,2–Benzisothiazol–3–ones and Vice Versa" Tetrahedron Letters, vol. 26, No. 14, pp 1753–1756, 1985. XP002004537. See especially p. 1755.

Baggaley et al: "Inhibitors of Blood Platelet Aggregation. Effoects of Some 1,2–Benzisothiazol–3–ones on Platelet Responsiveness to Adenosine Diphosphate and Collagen", J. Med. Chem 1985, vol. 28, No. 11, pp 1661–1667, XP002004538. see especially Table 1, enteries 19 and 26, and method d, p. 1666.

Lecher et al: "Some New Methods and preparing Bunte Salts", Journal of Organic Chemistry, vol. 20, 1955, pp. 475–487, XP002004539.

*Primary Examiner*—Laura L. Stockton
(74) *Attorney, Agent, or Firm*—Pillsbury Winthrop LLP

(57) ABSTRACT

A process for making a 2-alkylbenzisothiazolinone which comprises reacting a bisamide of formula

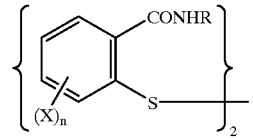

in water or an organic liquid containing water with a bisulphite or bisulphite release agent to form a Bunte salt and converting the Bunte salt under alkaline conditions to 2-alkyl-BIT. R is alkyl. Preferred substituents R are butyl, hexyl, 2-ethylbutyl and 2-ethylhexyl.

5 Claims, No Drawings

PROCESS FOR THE PREPARATION OF 1,2-BENZISOTHIAZOLIN-3-ONES

This is continuation of application Ser. No. 08/875,075, filed Jul. 17, 1997, now U.S. Pat. No. 5,936,094 which is a 371 of PCT/GB96/00427, Feb. 26, 1996.

The present invention relates to a process for making 1,2-benzisothiazolin-3-ones and to the use of compounds made thereby as industrial biocides.

1,2-Benzisothiazolin-3-ones (hereinafter "BIT") have long been known including their use as industrial biocides.

There exist three common methods for making BIT as disclosed in GB 848,130.

The first method involves making a 2-halogenothiobenzoyl halide and reacting this with a primary amine to obtain a N-substituted BIT. The 2-halogenothiobenzoyl halide is generally made by cleaving the disulphide bond of 2,2'-dithio-bis-benzoic acid with halogen and simultaneously or sequentially converting the carboxylic acid groups to acid halides.

A second method involves making a 2-halogenothiobenzamide and cyclising this compound in the present of acid or alkali. The 2-halogenothiobenzamide is typically made by converting 2,2'-dithio-bis-benzoic acid to bisamide and thereafter cleaving the disulphide bond with halogen. The halogen is often chlorine as provided by sulphuryl chloride.

A third method involves the disproportionation of 2,2'-dithio-bis-benzamides by heating in the presence of sodium hydroxide solution.

Owing to increasing environmental pressures there is a growing need to avoid processes involving the cleavage of the disulphide bond in bisamide precursors by halogen when making BIT's since these can given rise to pentahalophenols, especially pentachlorophenols. Thus, alternative methods of converting 2,2'-dithiobisamides (hereinafter "Bisamide") to BIT by non-halogen cyclisation have been sought.

One such method is the disproportionation of bisamide in alkali in the presence of oxygen or an oxygen release agent as disclosed in EP 187,349. This method gives high yields of BIT itself and 6-chloro-BIT. No examples of N-alkyl-BIT derivatives are recorded.

The disulphide bond of bisamides may also be cleaved using bisulphite which results in the formation of Bunte salts which may then be cyclised under alkaline conditions to give BIT's. Such a general reaction for making Bunte salts and BIT's has been disclosed by Tyrrell (Tetrahedron Letters 26 1753 (1985)) using bisamide precursors containing an amino substituent in the amide group. Only the one example is given in this disclosure where a 47% yield of the Bunte salt was obtained from a bisamide having a piperidinyl group in the amido substituent. The preparation of two further BIT derivatives containing a N-ethyl-piperidinyl and N-ethyl-pyrrolidinyl group have also been disclosed by Baggaley et al in J.Med.Chem 28 1661–1667, 1985 using the Bunte salt as intermediate but the overall yield of BIT from bisamide is again low at 22% and 21% yield, respectively. This preparative method does not appear to have been pursued further due possibly to the sensitivity of the method to the substituents found in the case of di-phenyl disulphide as disclosed by Lecher (et al) in J.O.C. 20 475 (1955). Here it is disclosed that good yields of Bunte salts were obtained in the case of bis-(3-nitrophenyl) disulphide, bis-(2-aminophenyl) disulphide, bis-(2-benzoylaminophenyl) disulphide and a poor yield from di-phenyl disulphide. No Bunte salt was identified from bis-(2-nitrophenyl) disulphide, bis-(2-methoxyphenyl) disulphide and 2,2'-dithiobis-benzothiazole. Because the yield of Bunte salts from di-phenyl disulphides is clearly influenced by the nature of the 2-substituent in particular there is no indication in Lecher whether the presence of 2-carbonamido groups as in bisamides will give high yields of Bunte salts.

We have now found that some bisamides can be converted to Bunte salts in high yield by reaction with bisulphite and especially a bisulphite-release agent and that the Bunte salts so obtained may be readily converted to BIT. The yield of N-alkyl-BIT using this process is higher than that obtained using the method disclosed in EP 187,349.

According to the present invention there is provided a process for making BIT of formula 1

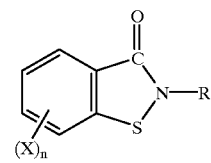

(1)

which comprises reacting a bisamide of formula 2

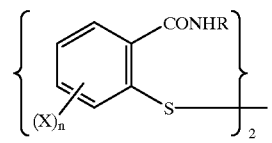

(2)

in water or an organic liquid containing water with a bisulphite or a bisulphite-release agent or a mixture thereof, wherein R is hydrogen, cycloalkyl, alkyl, alkyl substituted by hydroxy, halogen, $C_{1-6}$-alkoxy, carboxy, carbonamide, sulphonamide, nitrile or aryl or optionally substituted aryl;

X is halogen, nitro, alkoxy or nitrile; and n is from 0 to 4.

When R is alkyl it may be linear or branched and is preferably $C_{1-20}$-alkyl, more preferably $C_{1-12}$-alkyl and especially $C_{1-8}$-alkyl. Examples of such groups are methyl, ethyl, n-propyl, isopropyl, n-butyl, iso-butyl, tert-butyl, amyl, i-amyl, n-hexyl, i-hexyl, 2-ethylbutyl, n-heptyl, n-octyl, i-octyl, 2-ethylhexyl, n-decyl and n-dodecyl.

When R is cycloalkyl, the alicyclic ring preferably contains up to 8 carbon atoms such as cyclopropyl and especially cyclohexyl.

When R is aryl it preferably contains up to 10 carbon atoms and is especially phenyl.

When R is substituted aryl, the substituent may be as described for substituted alkyl.

When R is alkyl substituted by aryl, the aryl group is preferably phenyl and is especially benzyl and more especially 2-ethylphenyl. The phenyl ring in these substituted alkyl groups may itself be further substituted as described for substituted aryl but it is preferably unsubstituted.

Halogen means fluorine, iodine, bromine and especially chlorine.

Preferably n is zero.

The bisulphite-release agent may be any agent giving rise to bisulphite ion in aqueous media and is preferably sulphur dioxide in aqueous alkaline media and especially metabisulphite.

The reaction of the bisamide with a bisulphite or bisulphite-release agent may be catalysed by oxygen or a metal such as copper, iron and cobalt which may be present as a salt.

When R is H in the BIT of formula 1, the BIT may be prepared in the form of its salt with an alkali metal or ammonia. Examples of alkali metals are potassium and especially lithium or sodium.

It is especially preferred that R is unsubstituted alkyl or 2-ethylphenyl.

Good results have been obtained when R is methyl, n-butyl, n-hexyl, i-hexyl, n-octyl, 2-ethylphenyl, 2-ethylbutyl and 2-ethylhexyl.

The bisulphite or metabisulphite is preferably present in the form of a water-soluble salt such as an alkali metal or ammonium salt. Preferred alkali metals are lithium, potassium and especially sodium.

Metabisulphite is preferred since in many instances it gives higher yields of the Bunte salt and hence BIT.

The amount of bisulphite or bisulphite-release agent is preferably at least one mole and more preferably at least two moles for each mole of bisamide. Generally, there is no advantage in using a large excess of bisulphite or bisulphite-release agent. Thus, the amount of metabisulphite is preferably less than 8 moles and especially less than 5 moles of metabisulphite for each mole of bisamide. Higher yields of N-alkyl-BIT have been obtained with from 2.5 to 3 moles, for example 2.75 moles of metabisulphite for each mole of bisamide. In the case of bisulphite, the amount of bisulphite is preferably less than 10 moles and especially less than 8 moles bisulphite for each mole of bisamide.

As noted hereinbefore, water can be the medium in which the bisamide is reacted with bisulphite or bisulphite-release agent and this has been found an effective reaction medium for BIT itself (formula I, R is H) and N—$C_{1-2}$-alkyl-BIT's. However, for N-substituted-BIT's, the reaction medium is preferably an organic liquid.

The organic liquid may be hydrophilic or hydrophobic but is preferably hydrophilic.

When the organic liquid is hydrophobic it is preferably a solvent for the bisamide and may be an aliphatic hydrocarbon, chlorinated aliphatic hydrocarbon, an ether, ester or an aromatic hydrocarbon. Examples of hydrophobic organic liquids are methylene chloride, chloroform, carbon tetrachloride, trichloroethylene, perchloroethylene, trichloroethane, n-heptane, petroleum ether, diethyl ether, ethylacetate and toluene.

Where the organic liquid is hydrophobic the bisulphite or bisulphite-release agent may be dissolved in water and the bisamide converted to the Bunte salt by mixing the two phases. The Bunte salt is water soluble and is retained in the aqueous phase whereupon it may be readily separated by simple phase disengagement.

When the organic liquid is hydrophilic, it is preferably a glycol, ketone, carbitol, amide, sulphoxide and especially alcohol. Examples of such solvents are ethylene glycol, diethylene glycol, propylene glycol, acetone, methylethylketone, methyl and ethylcarbitol, dimethylformamide, dimethylacetamide, dimethylsulphoxide, methanol, ethanol, propanol, isopropanol, butanol, isobutanol and tert butanol including mixtures thereof. Methanol, ethanol and ethylene glycol are especially preferred, especially methanol.

It is also preferred that the hydrophilic liquid contains sufficient water to dissolve the bisulphite or bisulphite-release agent. In the case of bisulphite, the amount of water is preferably greater than 5%, more preferably greater than 10% and especially greater than 20% relative to the amount of organic liquid. It is also preferred that the amount of water is less than 100%, more preferably less than 70% and especially less than 50% relative to the weight of organic liquid.

In the case of metabisulphite, the amount of water is preferably at least 1% more preferably at least 2% and especially at least 4% relative to the weight of organic liquid. The amount of water is preferably less than 20%, more preferably less than 15% and especially less than 12% relative to the weight of organic liquid. Good results have been obtained when the amount of water relative to the organic liquid is from 6 to 10% and especially about 8%.

The bisulphite or metabisulphite may be added to the organic liquid as an aqueous solution or slurry but is preferably added in solid form to the bisamide in the organic liquid. This is particularly advantageous in the case of metabisulphite.

The formation of the Bunte salt is very facile and can be carried out by heating the bisamide, bisulphite and/or bisulphite-release agent in the organic liquid at temperatures below 100° C. For convenience, it is preferred to carry out the reaction under reflux in water, the organic liquid or organic liquid/water mix.

The Bunte salt may be isolated by any method known to the art such filtration or evaporation of the water, organic liquid or organic liquid/water mix. In one preferred method a hydrophobic liquid which is a non-solvent for the Bunte salt is added to remove the hydrophilic liquid or hydrophilic liquid/water mix as an azeotrope. Another preferred method, where the organic liquid is hydrophilic, is to add more water to effect separation/sedimentation of the Bunte salt. This latter method has been found particularly effective for N-alkyl-BIT's containing more than three carbon atoms in the alkyl chain.

Examples of preferred hydrophobic liquids which form azeotropic mixtures with water and/or hydrophilic liquid are xylene, toluene, hexane, cyclohexane and methylcyclohexane.

The preferred hydrophobic liquid which forms an azeotrophic is toluene.

The Bunte salt so obtained can be converted in high yield, which in most instances is quantitative, by treating the Bunte salt with alkali, especially aqueous alkali liquor. Preferably, the alkali is an alkali metal or ammonium hydroxide, carbonate or bicarbonate. Hydroxides are preferred. Preferred alkali metals are lithium, potassium and especially sodium.

The amount of alkali is relatively unimportant, but is generally a large excess relative to the amount of Bunte salt. It is preferred that the amount of alkali in the aqueous alkali liquor is sufficient to give a pH above 9, more preferably above 11 and especially above 13.

Cyclisation of the Bunte salt to form a BIT occurs rapidly in the presence of alkali and generally this reaction can be carried out at 20–30° C. Higher temperatures are not normally required.

When the Bunte salt has been isolated this can treated directly with aqueous alkali solution when the N-substituted BIT separates as either an oil or a solid.

When the Bunte salt is present in a hydrophobic liquid as a dispersion, this dispersion can be treated with aqueous alkali whereupon the BIT dissolves in the hydrophobic liquid on its formation. The BIT can then be isolated by removal of the hydrophobic liquid by any convenient method such as evaporation or steam stripping of the liquid.

Depending on the actual BIT and its subsequent commercial usage it is sometimes convenient to choose a hydrophobic liquid in which the BIT is to be subsequently formulated since this eliminates the need to first isolate the BIT.

As noted hereinbefore the bisamide is obtained from 2,2'-dithiobis-benzoic acid (hereinafter DTBA) which is often contaminated by polysulphides of formula 3

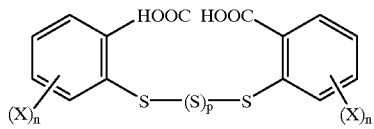

(3)

wherein X and n are as defined hereinbefore; and p is 1 or 2.

When the DTBA containing these polysulphides is converted to bisamide the bisamide also contains these polysulphide contaminants. On conversion of such bisamide to BIT using halogen to cleave the disulphide bond the presence of these polysulphides adversely affects the yield of BIT. The presence of polysulphides and other contaminants in the bisamide can also result in unacceptable discoloration of the BIT.

It has now been found that these polysulphides can also be reacted with bisulphite or bisulphite-release agent to give Bunte salts in high yield and that a BIT obtained from these polysulphides or bisamide containing polysulphides exhibits a more acceptable colour than that obtained when the disulphide bond is cleaved by halogen.

According to a further aspect of the invention there is provide a process for making BIT which comprises reacting a polysulphide of formula 4 or bisamide of formula 2 which contains a polysulphide of formula 4 in water, or an organic liquid containing water with bisulphite and/or metabisulphite or mixture thereof;

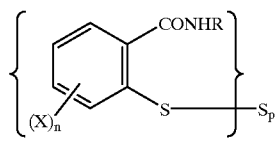

(4)

wherein

R, X, n and p are as hereinbefore defined.

When the polysulphide of formula 4 is present as a contaminant in the bisamide it is preferably less than 50%, more preferably less than 20% and especially less than 10% by weight relative to the weight of bisamide.

As noted hereinbefore, one of the methods for making a BIT is by reacting a 2-halogenothiobenzoyl halide with a primary amine or ammonia. The 2-halogenothiobenzoyl halide is made by cleaving the disulphide bond of DTBA with halogen and either simultaneously or sequentially forming the acid halide. If the DTBA contains polysulphides, then the reaction products with a primary amine or ammonia are a BIT and mixed bisamides of formulae 2 and 4. The yields of BIT are thereby reduced. It has now been found that these mixtures of BIT and mixed bisamides can be converted to high quality BIT by treating the mixture with sulphite or sulphite-release agent to convert the BIT and the mixed bisamides to their Bunte salts and subsequently treating the Bunte salt with alkali to form BIT.

According to a still further aspect of the invention there is provided a process for making a BIT of formula 1

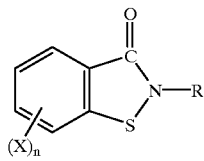

(1)

which comprises treating a mixture of BIT of formula 1 and bisamide of formula 5

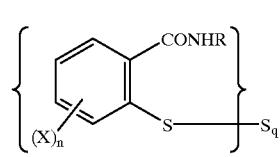

(5)

wherein

X, R and n are defined hereinbefore; and q is 0, 1 or 2;

in water or an organic liquid containing water with bisulphite or bisulphite-release agent or a mixture thereof.

BIT's are known industrial biocides and according to another aspect of the invention there is provided the use of BIT's made by the processes of this invention as industrial biocides, especially as fungicides and in particular as paint film fungicides and fungicides for plastics materials.

The invention is further described in more detail in the following examples wherein all references are to parts by weight unless indicated to the contrary.

EXAMPLE 1

Preparation of N-n-butyl-BIT using metabisulphite

A mixture of crude dithio-2,2'-bis(N-n-butylbenzamide) (60% dry weight bisamide and polysulphides, 13% by weight N-n-butyl benzisothiazolin-3-one, remainder unidentified) (12.8 parts), sodium metabisulphite (11.4 parts), methanol (59 parts) and water (5 parts) was heated and stirred at reflux for 4 hours. The reaction mix was then cooled stirred at 20–25° C. with decolorising carbon (0.5 parts) for 30 mins and then filtered. Toluene (65 parts) was added to the filtrate and the majority of the methanol/water was removed by azeotropic distillation whereupon the Bunte salt was obtained as a suspension in toluene. Water (100 parts) was added to the toluene suspension and the pH of the aqueous phase raised above 13.25 by addition of 47% sodium hydroxide solution. After stirring for 30 min at 20–25° C. the Bunte salt had completely cyclised to N-n-butyl-BIT which dissolved in the toluene phase. The toluene phase was separated, washed with water (2×25 parts) and the toluene removed by evaporation. N-n-butyl-BIT was obtained as a yellow oil (10.8 parts). Yield based on crude bisamide is 95% theory.

EXAMPLE 2

Preparation of N-n-butyl-BIT using bisulphite

A mixture of dithio-2,2'-bis-(N-n-butylbenzamide) (86.5% by dry weight, rest unidentified) (4.0 parts), methanol (15.6 parts) and sodium bisulphite solution (58.5% SO$_2$, 4.93 parts sodium bisulphite, 13.2 parts water) was heated and stirred at reflux for 2 hours. The reactants was then cooled, stirred with decolorising carbon (0.1 part) at 20–25°

C. for 10 minutes and filtered. The solid was washed with methanol/water (2:1) (10 parts) and the washing combined with the filtrate. 47% sodium hydroxide liquor was added to the filtrate to raise the pH above 13.5 and stirring continued for 30 mins at 20–25° C. to convert the Bunte salt to BIT. The BIT was then extracted into toluene (50 parts) and the toluene phase separated and washed with water (2×25 parts). Finally, the toluene was removed by distillation whereupon the N-n-butyl-BIT was recovered as a pale yellow oil (2.42 parts). Yield based on bisamide is 70% theory.

COMPARATIVE EXAMPLE A
Preparation of N-n-butyl-BIT using oxygen

A mixture of dithio-2,2'-bis(N-n-butylbenzamide) (58.8% dry weight bisamide, 9.2% N-n-butyl-BIT, remainder unidentified) (20.5 parts), water (200 parts), methanol (20 parts) and sodium hydroxide aqueous liquor (47% sodium hydroxide; 12.8 parts) were stirred at 55° C. for 24 hours whilst bubbling oxygen gas through the reaction mix at a rate of 3 ml gas per second.

The reactants were then cooled and the N-n-butyl-BIT extracted into dichloromethane (200 parts). The organic phase was separated, washed with water (2×110 parts) and dried over anhydrous sodium sulphate. The dichloromethane was then evaporated leaving the N-n-butyl-BIT as a dark oil (9.4 parts). Yield is 49.5%. This is a much lower yield than that obtained using the method of Example 2 and especially that of Example 1.

EXAMPLE 3
Preparation of N-n-hexyl-BIT using metabisulphate

Crude dithio-2,2'-bis(N-n-hexylbenzamide) (30 parts at 99% strength, 0.063M) was dissolved in methanol (155 parts). Water (13.1 parts) and sodium metabisulphate (31.1 parts) was added and the reactants stirred at reflux for 6 hours. The reactants were then cooled, toluene (169 parts) were added and the majority of the methanol and water was removed as an azeotrope by heating whereupon the Bunte salt was obtained as a suspension in toluene. Water (155 parts) was added followed by caustic soda liquor (43.3 parts, 47% (w/w) strength) and the reactants stirred for 1 hour at 40–45° C., when the Bunte salt cyclised to form N-n-hexyl-BIT which dissolved in the toluene phase.

Activated carbon (1.13 parts) in water (16 parts) was then added and the reactants stirred for a further 40 minutes at 40–45° C. After screening, the toluene layer was removed, washed with water and finally the toluene removed by distillation. The product was obtained as a pale yellow oil (24.72 parts at 96.8% strength; 80.3% theory).

EXAMPLE 4
Preparation of N-2-ethylhexyl-BIT using metabisulphate

This was prepared by a similar process to that described in Example 3 above except using dithio-2,2'-bis(N-2-ethylhexylbenzamide) (29.78 parts, 0.063 M) in place of the butyl analogue. The product was obtained as a pale oil (23.93 parts, 70.3% theory).

EXAMPLE 5
Preparation of N-2-ethylbutyl-BIT using metalbisulphate

This was also prepared by a similar process to that described in Example 3 except using dithio-2,2'-bis(N-2-ethylbutylbenzamide) (20.3 parts, 0.043M) and sodium metabisulphate () 16.35 parts) in place of the butyl analogue and the amount of metabisulphate in this example.

The product was obtained as a dark yellow oil which solidified on standing (12.0 parts, 50% theory). The yield of BIT in this example was reduced owing to filtration of the toluene phase after cyclisation of the benzamide precursor to form the BIT which removed product.

What is claimed is:

1. A process for making BIT of formula 1

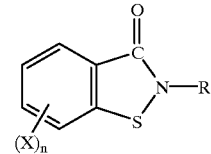

(1)

which comprises reacting a bisamide of formula 5

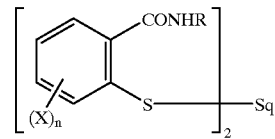

(5)

wherein,
R is cycloalkyl containing from 3 to 8 carbons atoms or $C_{1-20}$-alkyl optionally substituted by phenyl;
X is halogen, nitro, alkoxy or nitrile;
n is 0 to 4; and
q is 0, 1, or 2
in water or an organic liquid containing water with metabisulphite.

2. A process as claimed in claim 1, wherein n is zero.

3. A process as claimed in claim 1, wherein R is $C_{1-12}$-alkyl optionally substituted by phenyl.

4. A process as claimed in claim 1, wherein R is methyl, n-butyl, n-hexyl, n-octyl, 2-ethylbutyl, 2-ethyl-hexyl, i-hexyl or 2-phenylethyl.

5. A process as claimed in claim 1 wherein, the organic liquid is methanol.

* * * * *